(12) United States Patent
Baroni et al.

(10) Patent No.: US 7,326,720 B2
(45) Date of Patent: Feb. 5, 2008

(54) PHENYL- AND PYRIDYLPIPERIDINES WITH TNF ACTIVITY

(75) Inventors: Marco Baroni, Vanzago-Milan (IT); Bernard Bourrie, Saint-Gely-du-Fesc (FR); Pierre Casellas, Montpellier (FR)

(73) Assignee: Sanofi-Aventis, Paris (FR)

( * ) Notice: Subject to any disclaimer, the term of this patent is extended or adjusted under 35 U.S.C. 154(b) by 585 days.

(21) Appl. No.: 10/475,272

(22) PCT Filed: Apr. 19, 2002

(86) PCT No.: PCT/FR02/01342

§ 371 (c)(1),
(2), (4) Date: Oct. 20, 2003

(87) PCT Pub. No.: WO02/085887

PCT Pub. Date: Oct. 31, 2002

(65) Prior Publication Data

US 2004/0127517 A1   Jul. 1, 2004

(30) Foreign Application Priority Data

Apr. 20, 2001 (FR) .................................. 01 05361

(51) Int. Cl.
*A61K 31/4523* (2006.01)
*A61K 31/4545* (2006.01)
*C07D 211/06* (2006.01)
*C07D 211/08* (2006.01)

(52) U.S. Cl. ....................... 514/318; 514/320; 514/321; 514/322; 546/193; 546/208; 546/209; 546/210

(58) Field of Classification Search ................ 546/193, 546/208, 209, 210; 514/318, 320, 321, 322
See application file for complete search history.

(56) References Cited

U.S. PATENT DOCUMENTS

| 4,455,422 | A | * | 6/1984 | Banno et al. ................ 544/363 |
| 4,460,593 | A | | 7/1984 | Banno et al. |
| 4,567,187 | A | | 1/1986 | Banno et al. |
| 4,619,932 | A | | 10/1986 | Banno et al. |

FOREIGN PATENT DOCUMENTS

FR   2 477 542   9/1981

OTHER PUBLICATIONS

Dukic, Sladjana et al., "Synthesis and dopaminergic properties of 3- and 4-substituted 1-{2-'5-(1H-benzimidazole-2-thione)ethyl}piperidines and related compounds, " Archiv der Pharmazie, 1997, 330(½), 25-28.*

Accession No. 1997:247645, CAPLUS listing of Dukic et al, "Synthesis and dopaminergic properties of 3- and 4-substituted 1-{2-'5-(1H-benzimidazole-2-thione)ethyl}piperidines and related compounds, " archive der Pharmazie, 1997, 330(½), 25-28.*

Dukic, Sladjana et al., "Synthesis and dopaminergic properties of 3- and 4-substituted 1-{2-'5-(1H-benzimidazole-2-thione)!ethyl} piperidines and related compounds"; Arch. Pharm. (Weinheim, Ger.); 1997; 330(½), 25-28; XP002189144.

Bourrie, Bernard et al., "The neuroprotective agent SR57746A abrogates experimental autoimmune encephalomyelitis and impairs associated blood-brain barrier disruption: implications for multiple sclerosis treatment"; Proc. Natl. Acad. Sci. U.S.A.; 1999; 96(22). 12855-12859.

* cited by examiner

*Primary Examiner*—Kamal Saeed
*Assistant Examiner*—Janet L. Coppins
(74) *Attorney, Agent, or Firm*—Robert J. Kajubi; Paul E. Dupont

(57) ABSTRACT

The present invention relates to compounds of formula (I):

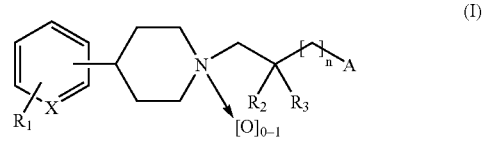

in which X represents N or CH; $R_1$ represents a hydrogen or halogen atom or a $CF_3$ group; $R_2$ and $R_3$ independently represent a hydrogen atom or a methyl group; n is 0 or 1; A represents a condensed heterocyclic group of formula (w)

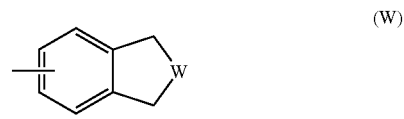

where W completes an aromatic or saturated 6-membered ring system comprising one or two nitrogen atoms or else an aromatic or saturated 5-membered ring system comprising a nitrogen, oxygen or sulfur atom which are optionally substituted, and to their N-oxides and to their salts or solvates, to the pharmaceutical compositions and the medicaments comprising them and to a process for their preparation.

36 Claims, No Drawings

PHENYL- AND PYRIDYLPIPERIDINES WITH TNF ACTIVITY

The present invention relates to novel phenyl- and pyridylpiperidines, to the pharmaceutical compositions comprising them and to a process for their preparation.

U.S. Pat. No. 5,118,691 and U.S. Pat. No. 5,620,988 disclose tetrahydropyridines substituted by a quinolyl-3-alkyl radical which show a dopaminergic activity.

FR 2 477 542 discloses piperidines and piperazines substituted by carbostyrils which have a mainly antihistaminic activity.

Dukic S. et al. (Arch. Pharm., 1997, 330 (½), 25-28) disclose phenylpiperidines carrying a benzimidazol-5-yl-ethyl substituent which show a dopaminergic activity.

It has now been found that some phenyl- and pyridylpiperidines substituted by heterocyclic radicals have a powerful activity with regard to modulating TNF-α (Tumor Necrosis Factor).

TNF-α is a cytokine which has recently aroused interest as mediator of immunity, inflammation, cell proliferation, fibrosis, and the like. This mediator is extensively present in inflamed synovial tissue and exerts an important role in the pathogenesis of autoimmunity (Annu. Rep. Med. Chem., 1997, 32, 241-250).

Thus, the present invention relates, according to one of its aspects, to piperidines of formula (I):

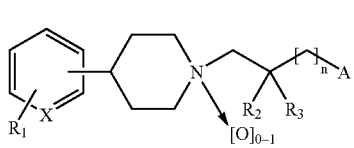

in which
X represents N or CH;
$R_1$ represents a hydrogen or halogen atom or a $CF_3$ group;
$R_2$ and $R_3$ independently represent a hydrogen atom or a methyl group;
n is 0 or 1;
A represents a condensed heterocyclic group of formula (w)

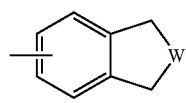

where W completes
either an aromatic or saturated 6-membered ring system comprising one or two nitrogen atoms, it being possible for the ring system to be substituted by one or two halogen atoms or one or two ($C_1$-$C_4$) alkyl, ($C_1$-$C_4$) alkoxy or $CF_3$ groups;
or an aromatic or saturated 5-membered ring system comprising a nitrogen, oxygen or sulfur atom, it being possible for the ring system to be substituted by one or two ($C_1$-$C_4$) alkyl groups; and to their N-oxides and to their salts or solvates.

In the present description, the term "($C_1$-$C_4$) alkyl" denotes a monovalent radical of a saturated, straight- or branched-chain, $C_1$-$C_4$ hydrocarbon and the term "($C_1$-$C_4$) alkoxy" denotes a monovalent radical of a saturated, straight- or branched-chain, $C_1$-$C_4$ hydrocarbon bonded via an oxygen atom.

In the present description, the term "halogen" denotes an atom chosen from chlorine, bromine, iodide and fluorine.

Preferred compounds are those where n is zero.

Other preferred compounds are those where $R_2$ and $R_3$ are each H.

Other preferred compounds are those where $R_1$ is a $CF_3$ group.

Other preferred compounds are those where $R_1$ is a fluorine atom.

Other preferred compounds are those where X is CH and $R_1$ is in the 2- or 3-position of the benzene.

Other preferred compounds are those where X is CH and $R_1$ is a $CF_3$ group.

Other preferred compounds are those where X is a nitrogen atom and the pyridine is substituted in the 2,6-positions.

Particularly preferred compounds are the compounds of formula (I) where A is chosen from quinoline, isoquinoline, quinoxaline, cinnoline and phthalazine, optionally substituted by one or two ($C_1$-$C_4$) alkyl groups.

Particularly preferred compounds are the compounds of formula (I) where A is chosen from indole, benzothiophene and benzofuran.

According to a preferred aspect, a subject matter of the invention is the compounds of formula (I) where A is a group of formula (a) or (b):

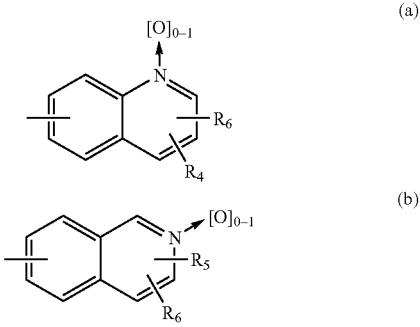

where
$R_4$ represents a hydrogen or halogen atom, a ($C_1$-$C_4$) alkyl group, a $CF_3$ group or an amino, mono($C_1$-$C_4$)alkylamino or di($C_1$-$C_4$)alkylamino group;
$R_5$ represents a hydrogen or halogen atom, a ($C_1$-$C_4$) alkoxy group, a ($C_1$-$C_4$) alkyl group or a $CF_3$ group;
$R_6$ represents a hydrogen atom, a ($C_1$-$C_4$) alkyl group or a ($C_1$-$C_4$) alkoxy group; and their salts or solvates.

Particularly preferred compounds are the compounds of formula (I) where A is a group of formula (a) or (b) and $R_4$, $R_5$ and $R_6$ are hydrogen atoms.

According to the present invention, the compounds of formula (I) can exist as N-oxide derivatives. As indicated in the above formula, the compounds of formula (I) can in particular carry the N-oxide group on the piperidine or else on the nitrogens of the groups (w), (a) and (b) or else all the nitrogens present can be simultaneously oxidized.

The salts of the compounds of formula (I) according to the present invention comprise both addition salts with pharmaceutically acceptable inorganic or organic acids, such as the hydrochloride, hydrobromide, sulfate, hydrogensulfate, dihydrogen-phosphate, citrate, maleate, tartrate, fumarate, gluconate, methanesulfonate, 2-naphthalenesulfonate, and the like, and addition salts which make possible suitable separation or crystallization of the compounds of formula (I), such as the picrate or oxalate, or addition salts with optically active acids, for example camphorsulfonic acids and mandelic or substituted mandelic acids.

The optically pure stereoisomers and the mixtures of isomers of the compounds of formula (I) due to the asymmetric carbon, when one of $R_2$ and $R_3$ is a methyl and the other a hydrogen, in any proportion, form part of the present invention.

The compounds of formula (I) can be prepared by a condensation/reduction reaction starting from a compound of formula (II):

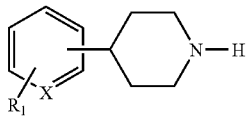

(II)

in which X and $R_1$ are as defined above, with an aldehyde of formula (III):

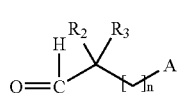

(III)

in which $R_2$, $R_3$, n and A are as defined above, isolation of the compound of formula (I) and optional conversion to one of its salts or solvates or to its N-oxide derivatives.

The condensation/reduction reaction is carried out by mixing the starting compounds (II) and (III) in an organic solvent, such as an alcohol, such as, for example, methanol, in an acidic medium, in the presence of a reducing agent, such as sodium cyanoborohydride, according to conventional methods.

If desired, it is also possible to use, instead of the starting piperidines (II), the corresponding 1,2,3,6-tetrahydropyridine derivatives and to reduce the double bond after the condensation according to well-known methods.

Alternatively, the compounds of formula (I) can be prepared by a process which plans
(a) to react the compound of formula (II):

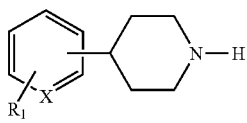

(II)

in which X and $R_1$ are defined as above, with a functional derivative of the acid of formula (IV):

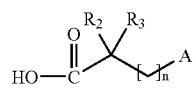

(IV)

in which $R_2$, $R_3$, n and A are as defined above, (b) to reduce the carbonyl group of the compound of formula (V) thus obtained:

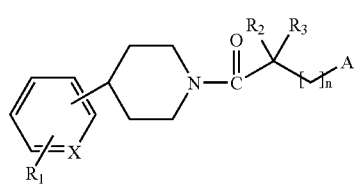

(V)

(c) to isolate the compound of formula (I) thus obtained and, optionally, to convert it to one of its salts or solvates or to its N-oxide derivatives.

The reaction of stage (a) can be suitably carried out in an organic solvent at a temperature of between −10° C. and the reflux temperature of the reaction mixture.

It may be preferable to carry out the reaction under cold conditions when it is exothermic, as in the case where the chloride is used as functional derivative of the acid of formula (IV).

Use may be made, as appropriate functional derivative of the acid of formula (IV), of the free acid, which is optionally activated (for example with BOP=tri(dimethylamino)benzotriazol-1-yloxyphosphonium hexafluorophosphate), an anhydride, a mixed anhydride, an active ester or an acid halide, preferably the bromide. Among the active esters, the p-nitrophenyl ester is particularly preferred but the methoxyphenyl, trityl, benzhydryl and similar esters are also suitable.

Use is preferably made, as reaction solvent, of a halogenated solvent, such as methylene chloride, dichloroethane, 1,1,1-trichloroethane, chloroform and the like, but also other organic solvents compatible with the reactants employed, for example dioxane, tetrahydrofuran or a hydrocarbon, such as hexane, or even dimethylformamide (DMF), can likewise be employed.

The reaction can be suitably carried out in the presence of a proton acceptor, for example of an alkaline carbonate or of a tertiary amine, such as triethylamine (TEA).

The reduction of stage (b) can be suitably carried out with appropriate reducing agents, such as borane complexes, for example borane-dimethyl sulfide ($[CH_3]_2$S—$BH_3$), aluminum hydrides or a complex hydride of lithium and of aluminum, in an inert organic solvent at a temperature of between 0° C. and the reflux temperature of the reaction mixture, according to conventional techniques.

The term "inert organic solvent" is understood to mean, in the present invention, a solvent which does not interfere with the reaction. Such solvents are, for example, ethers, such as diethyl ether, tetrahydrofuran (THF), dioxane or 1,2-dimethoxyethane.

According to a preferred procedure, the reduction is carried out with borane-dimethyl sulfide, used in excess with respect to the starting compound (III), at the reflux temperature optionally under an inert atmosphere. The reduction is normally completed after a few hours.

It has been noticed that, for some products, in particular when W completes a 6-membered aromatic ring system comprising 1 or 2 nitrogen atoms, the reaction of stage (b) above can also result in the reduction of said ring system A, in particular in the part completed by W. Consequently, if it is not desired to obtain the partial reduction of the ring system A, it is then advisable to carry out the synthesis of such compounds according to the condensation/reduction reaction described above by using sodium cyanoborohydride as reducing agent, so as to safeguard the aromatic ring systems.

It is also possible to synthesise the products of formula (I) where A is a group (a) or (b) by reduction of the corresponding 1,2,3,6-tetra-hydropyridine derivatives, which are disclosed in WO 01/29026, under the reduction conditions described above.

The desired compound is isolated according to conventional techniques in the free base form or in the form of one of its salts. The free base can be converted to one of its salts by simple salification in an organic solvent, such as an alcohol, preferably ethanol or isopropanol, an ether, such as 1,2-dimethoxyethane, ethyl acetate, acetone or a hydrocarbon, such as hexane.

The compound of formula (I) obtained is isolated according to conventional techniques and is optionally converted to one of its salts or solvates or to its N-oxide derivatives.

The starting compounds of formulae (II), (III) and (IV) are known or else they can be prepared analogously to known compounds. Such products are disclosed, for example, in WO 97/01536; J. Am. Chem. Soc., 1948, 70, 2843-2847; J. Med. Chem., 1997, 40 (7), 1049.

The compounds of formula (III) can, for example, be prepared by heating the trifluoromethylsulfonyl derivative (otherwise called "triflate") of the compound of formula A—OH with N,N-dialkylethanolamine vinyl ether in the presence of a palladium catalyst and of a strong base, such as, for example, triethylamine, and by reacting the intermediate thus obtained with concentrated sulfuric acid, according to conventional procedures. Examples of such a process are reported in the experimental part. Alternatively, the aldehydes of formula (III) can be prepared by reduction of the corresponding acids of formula (IV) according to well-known methods.

The compounds of formula (I) carrying an N-oxide group on the nitrogen atoms of the groups (w), (a) and (b) can be prepared from the N-oxide derivatives of the compounds of formula (III) or (IV).

The compounds of formula (I) carrying an N-oxide group on the nitrogen atom of the piperidine can be prepared by oxidation of the corresponding compounds of formula (I). In this case, the compound of formula (I) as obtained by the above syntheses is subjected to an oxidation reaction according to conventional methods, for example to a reaction with m-chloroperbenzoic acid, in a suitable solvent, and is isolated according to conventional techniques well known to a person skilled in the art.

The compounds of the invention have properties which are advantageous with respect to the inhibition of TNF-α.

These properties were demonstrated using a test aimed at measuring the effect of molecules on TNF-α synthesis induced in Balb/c mice by lipopolysacchande (LPS) of *Escherichia coli* (O55:B5, Sigma, St Louis, Mo.).

The products to be tested are administered orally to groups of 5 female Balb/c mice (Charles River, France) aged from 7 to 8 weeks. One hour later, the LPS is administered intravenously (10 μg/mouse). A blood sample is taken from each animal 1.5 hours after administration of the LPS. The samples are centrifuged and the plasma is recovered and frozen at −80° C. The TNF-α is measured using commercial kits (R and D, Abingdon, UK).

In this test, compounds representative of the invention proved to be very active, inhibiting TNF-α synthesis even at very low doses.

Due to this activity and to their low toxicity, the compounds of formula (I) and its salts or solvates can indeed be used in the treatment of diseases related to immune and inflammatory disorders or as analgesics. In particular, the compounds of formula (I) can be used to treat atherosclerosis, autoimmune diseases, diseases which lead to the demyelinization of neurones (such as multiple sclerosis), asthma, rheumatoid arthritis, fibrotic diseases, idiopathic pulmonary fibrosis, cystic fibrosis, glumerulonephritis, rheumatoid spondylitis, osteoarthritis, gout, bone and cartilage resorption, osteoporosis, Paget's disease, multiple myeloma, uveoretinitis, septic shock, septicemia, endotoxic shock, graft-versus-host reaction, graft rejection, adult respiratory distress syndrome, silicosis, asbestosis, pulmonary sarcoidosis, Crohn's disease, ulcerative colitis, amyotrophic lateral sclerosis, Alzheimer's disease, Parkinson's disease, lupus erythematosus disseminatus, hemodynamic shock, ischemic pathological conditions (myocardial infarction, myocardial ischemia, coronary vasospasm, angina pectoris, cardiac insufficiency, heart attack), postischemic reperfusion injuries, malaria, mycobacterial infections, meningitis, leprosy, viral infections (HIV, cytomegalovirus, herpes virus), AIDS-related opportunistic infections, tuberculosis, psoriasis, atopic and contact dermatosis, diabetes, cachexia, cancer and radiation-mediated damage.

The compounds of formula (I) and their pharmaceutically acceptable salts and solvates are preferably administered orally.

In the oral pharmaceutical compositions of the present invention, the active principle can be administered in unit administration forms, as a mixture with conventional pharmaceutical carriers, to animals and human beings for the treatment of the abovementioned conditions. The appropriate unit administration forms comprise, for example, tablets, optionally scored, gelatin capsules, powders, granules and solutions or suspensions to be taken orally.

When a solid composition is prepared in the form of tablets, the main active ingredient is mixed with a pharmaceutical vehicle, such as gelatin, starch, lactose, magnesium stearate, talc, gum arabic or the like. The tablets can be coated with sucrose or other appropriate materials or they can be treated so that they have a prolonged or delayed activity and so that they continuously release a predetermined amount of active principle.

A preparation in the form of gelatin capsules is obtained by mixing the active ingredient with a diluent and by pouring the mixture obtained into soft or hard gelatin capsules.

A preparation in the syrup or elixir form can comprise the active ingredient in conjunction with a sweetener, preferably a calorie-free sweetener, methylparaben and propylparaben as antiseptics, and an appropriate colorant and flavoring.

The water-dispersible powders or granules can comprise the active ingredient as a mixture with dispersing agents, wetting agents or suspending agents, such as polyvinylpyrrolidone, and with sweeteners or flavor enhancers.

The active principle can also be formulated in the form of microcapsules, optionally with one or more carriers or additives.

In the pharmaceutical compositions according to the present invention, the active principle can also be in the form of an inclusion complex in cyclodextrins, their ethers or their esters.

The amount of active principle to be administered depends, as always, on the degree of progression of the disease and also on the age and weight of the patient. Nevertheless, the unit doses generally comprise from 0.001 to 100 mg, better still from 0.01 to 50 mg, preferably from 0.1 to 20 mg, of active principle, advantageously from 0.5 to 10 mg.

According to another of its aspects, the present invention relates to a combination comprising a compound of formula (I) or one of its pharmaceutically acceptable salts or solvates and at least one compound chosen from immunosuppressants, such as interferon beta-1b; adrenocorticotropic hormone; glucocorticoids, such as prednisone or methylprednisolone; or interleukin-1 inhibitors.

More particularly, the invention relates to a combination comprising a compound of formula (I) or one of its pharmaceutically acceptable salts or solvates and at least one compound chosen from roquinimex (1,2-dihydro-4-hydroxy-N,1-dimethyl-2-oxo-3-quinolinecarboxanilide), myloran (product from Autoimmune comprising bovine myelin), antegren (monoclonal human antibody from Elan/Athena Neurosciences) or recombinant interferon beta-lb.

Other possible combinations are those composed of a compound of formula (I) or one of its pharmaceutically acceptable salts or solvates and a potassium-channel blocker, such as, for example, fampridine (4-aminopyridine).

According to another of its aspects, the invention relates to a method for the treatment of diseases related to immune and inflammatory disorders and in the treatment of pain, in particular atherosclerosis, autoimmune diseases, diseases which lead to the demyelinization of neurones (such as multiple sclerosis), asthma, rheumatoid arthritis, fibrotic diseases, idiopathic pulmonary fibrosis, cystic fibrosis, glumerulonephritis, rheumatoid spondylitis, osteoarthritis, gout, bone and cartilage resorption, osteoporosis, Paget's disease, multiple myeloma, uveoretinitis, septic shock, septicemia, endotoxic shock, graft-versus-host reaction, graft rejection, adult respiratory distress syndrome, silicosis, asbestosis, pulmonary sarcoidosis, Crohn's disease, ulcerative colitis, amyotrophic lateral sclerosis, Alzheimer's disease, Parkinson's disease, lupus erythematosus disseminatus, hemodynamic shock, ischemic pathological conditions (myocardial infarction, myocardial ischemia, coronary vasospasm, angina pectoris, cardiac insufficiency, heart attack), postischemic reperfusion injuries, malaria, mycobacterial infections, meningitis, leprosy, viral infections (HIV, cytomegalovirus, herpes virus), AIDS-related opportunistic infections, tuberculosis, psoriasis, atopic and contact dermatosis, diabetes, cachexia, cancer and radiation-mediated damage, comprising the administration of a compound of formula (I) or of one of its pharmaceutically acceptable salts or solvates, alone or in combination with other active principles.

The following examples illustrate the invention.

Preparation 7-isoquinolylacetaldehyde 1.5 g (0.0103 mol) of 7-hydroxyisoquinoline and 5.3 ml of pyridine are cooled to 0° C. 1.86 ml of triflic anhydride are added thereto dropwise. The mixture is stirred at 0° C. for 1 hour and then at ambient temperature for 2 hours. It is poured into a water/ice mixture and extracted with ethyl acetate, the organic phase is dried and the solvent is evaporated under reduced pressure. The crude product is purified by chromatography on a column of silica gel, elution being carried out with a cyclohexane/ethyl acetate=7/3 mixture. 7-Hydroxyisoquinoline trifluoromethanesulfonate is obtained in the form of an oil. 1.65 g of this product are mixed under argon with 27.5 ml of anhydrous dimethylformamide, 41 mg of palladium acetate, 1.65 ml of anhydrous triethylamine and 1.38 g of N,N-diethylethanolamine vinyl ether. The mixture is heated at 80° C. for 36 hours. It is poured into a water/ethyl acetate mixture, the two phases are separated, the organic phase is washed with water and dried, and the solvent is evaporated under reduced pressure. The residue is purified by chromatography on a column of silica gel, elution being carried out with an ethyl acetate/methanol=9/1 mixture. 2-[2-(7-Isoquinolyl)ethenyl)oxy)]-N,N-diethyl-1-ethanamine is obtained. 1.5 g of this product are treated with 130 ml of water and 13 ml of 96% sulfuric acid. The mixture is heated at 60° C. for 4.5 hours and is poured into ice, a saturated aqueous NaHCO$_3$ solution is added thereto and extraction is carried out with ethyl acetate. The organic phase is dried and the solvent is evaporated under reduced pressure. The title compound is obtained.

EXAMPLE 1

7-(2-(4-(3-(Trifluoromethyl)phenyl)piperidino)-ethyl)isoquinoline and its dihydrochloride dihydrate 1a. 7-(2-(4-(3-(Trifluoromethyl)phenyl)-1,2,3,6-tetrahydropyrid-1-yl) ethyl)isoquinoline and its dihydrochloride dihydrate 1.75 g (0.0077 mol) of 4-(3-(trifluoromethyl)phenyl)-1,2,3,6-tetrahydropyridine, 30 ml of methanol, 1.15 ml of glacial acetic acid and 0.73 g of anhydrous ethyl acetate are mixed. The mixture is cooled to 0-5° C. and 1.14 g of 7-isoquinolylacetaldehyde (as obtained according to the Preparation) and, with care, 1.1 g (0.0175 mol) of sodium cyanoborohydride are added thereto. The mixture is stirred at 0-5° C. for 1.5 hours and subsequently at ambient temperature overnight. 7 ml of concentrated hydrochloric acid are added, the mixture is stirred for 10 minutes, the solvent is evaporated under reduced pressure and the residue is taken up in an ethyl acetate/dilute NH$_4$OH mixture. The organic phase is dried over sodium sulfate and filtered, and the solvent is evaporated. The residue is purified on a column of silica gel, elution being carried out with an ethyl acetate/methanol=9/1 mixture. The title compound is obtained. The dihydrochloride is prepared using a solution of isopropanol saturated with hydrochloric acid. 1.1 g of product are obtained.

M.p. (dihydrochloride dihydrate) 230-233° C.

1b. 7-(2-(4-(3-(Trifluoromethyl)phenyl)piperidino)-ethyl)isoquinoline and its dihydrochloride dihydrate 220 mg of the product from the preceding stage are dissolved in 20 ml of ethanol, 30 mg of Pd/C are added thereto and the mixture is hydrogenated at atmospheric pressure at 45° C. for 6 hours. The catalyst is filtered off and the solvent is evaporated under reduced pressure. The residue is crystallized from isopropanol and 150 mg of the title compound are obtained.

M.p. (dihydrochloride dihydrate) 223-225° C.

EXAMPLE 2

6-(2-(4-(3-(Trifluoromethyl)phenyl)piperidino)ethyl)-1,2,3,4-tetrahydroisoquinoline and its dihydrochloride 400 mg (0.08 mmol) of 6-(2-(4-(3-(trifluoromethyl)phenyl)tetrahydropyrid-1-yl)ethyl)isoquinoline hydrochloride (prepared according to the procedures disclosed in WO 01/29026) are dissolved in 40 ml of 90% ethanol, and 40 mg of 10% Pd/C are added thereto. The mixture is hydrogenated at atmospheric pressure and at a temperature of 45° C. for 4 hours. The catalyst is subsequently filtered off and the solvent is evaporated, producing the title product, which is crystallized from isopropanol. The product is filtered off in the form of a white solid.

M.p. 299-300° C.

EXAMPLE 3

6-(2-(4-(3-(Trifluoromethyl)phenyl)piperidino)ethyl)-1,2,3,4-tetrahydroquinoxaline dihydrochloride 3a. 2-(Quinoxalin-6-yl)-1-(4-(3-(trifluoromethyl)-phenyl)piperidino)ethanone 0.48 g (2.55 mmol) of quinoxalin-6-ylacetic acid is mixed in 25 ml of DMF, and 1.07 ml of TEA, 0.68 g (2.55 mmol) of 4-(3-(trifluoromethyl)phenyl)piperidine hydrochloride and 1.13 mg of BOP are added thereto. The mixture is heated at ambient temperature overnight, 200 ml of water are added and extraction is carried out with ethyl acetate. The organic phase is dried over sodium sulfate and filtered, and the solvent is evaporated under reduced pressure. A dark oil is thus obtained, which oil is purified by flash chromatography on a column of silica gel, elution being carried out with ethyl acetate. 0.76 g of the title product is obtained in the form of a yellow oil.

3b. 6-(2-(4-(3-(Trifluoromethyl)phenyl)piperidino)-ethyl)-1,2,3,4-tetrahydroquinoxaline and its dihydrochloride 0.75 g of the product from the preceding stage is dissolved under a stream of nitrogen in 25 ml of THF and the solution is cooled to 0° C. 3.76 ml of LiAlH$_4$ (1M solution in THF) are added thereto portionwise. The mixture is stirred at ambient temperature overnight and then water is added thereto to bring the reaction to an end. Extraction is carried out with ethyl acetate, the organic phase is dried over sodium sulfate and filtered, and the solvent is evaporated under reduced pressure. A dark oil is obtained, which oil is purified by flash chromatography on a column of silica gel, elution being carried out with a methanol/ethyl acetate=1/1 mixture. The dihydrochloride is prepared with isopropanol saturated with hydrochloric acid. The solvent and excess hydrochloric acid are evaporated under reduced pressure and the title product is thus obtained in the form of a glassy solid.

M.p. 86-87° C.

EXAMPLES 4-6

The following compounds of formula (I) are prepared according to the procedure described in example 3:

| Ex. | R1 | X | A | M.p. |
|---|---|---|---|---|
| 4 | CF$_3$ | CH | 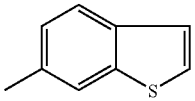 | 158–161° C. (oxalate) |
| 5 | CF$_3$ | CH | (quinoline) | 217–221° C. (hydrochloride) |
| 6 | CF$_3$ | CH | (benzothiophene) | 150–154° C. (oxalate) |

Note:
In example 5, the reduction of stage (b) was carried out with borane-dimethyl sulfide ([CH$_3$]$_2$S—BH$_3$) instead of LiAlH$_4$.

EXAMPLES 7-9

The following compounds of formula (I) are prepared according to the procedure described in example 1a, using appropriate aldehydes and using piperidine derivatives instead of 4-(3-(trifluoromethyl)phenyl)-1,2,3,6-tetrahydropyridine:

| Ex. | R1 | X | A | M.p. |
|---|---|---|---|---|
| 7 | H | CH | (isoquinoline) | 109–111° C. (free base) |
| 8 | CF$_3$ | CH | (isoquinoline) | 105–108° C. (oxalate) |
| 9 | CF$_3$ | N | (isoquinoline) | 87–90° C. (oxalate) |

What is claimed is:

1. A compound of formula (I):

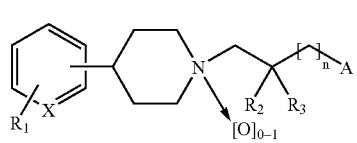

in which
X represents N or CH;
R$_1$ represents a hydrogen or halogen atom or a CF$_3$ group;
R$_2$ and R$_3$ independently represent a hydrogen atom or a methyl group;
n is 0 or 1;
A represents a condensed heterocyclic group of formula (w)

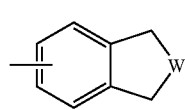

(W)

where W completes
- either an aromatic or saturated 6-membered ring system comprising one or two nitrogen atoms, it being possible for the ring system to be substituted by one or two halogen atoms or one or two $(C_1\text{-}C_4)$ alkyl, $(C_1\text{-}C_4)$ alkoxy or $CF_3$ groups;
- or an aromatic or saturated 5-membered ring system comprising a nitrogen, oxygen or sulfur atom, it being possible for the ring system to be substituted by one or two $(C_1\text{-}C_4)$ alkyl groups;

or an N-oxide, salt or solvate thereof.

2. A compound according to claim 1, where A represents a group of formula (a) or (b)

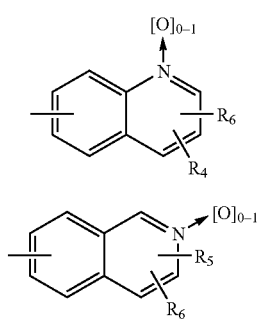

where
- $R_4$ represents a hydrogen or halogen atom, a $(C_1\text{-}C_4)$ alkyl group, a $CF_3$ group or an amino, mono$(C_1\text{-}C_4)$alkylamino or di$(C_1\text{-}C_4)$alkylamino group;
- $R_5$ represents a hydrogen or halogen atom, a $(C_1\text{-}C_4)$ alkoxy group, a $(C_1\text{-}C_4)$ alkyl group or a $CF_3$ group; and
- $R_6$ represents a hydrogen atom, a $(C_1\text{-}C_4)$ alkyl group or a $(C_1\text{-}C_4)$ alkoxy group.

3. A compound according to claim 1, where A is chosen from benzofuran, benzothiophene, indole, quinoxaline, cinnoline and phthalazine, optionally substituted by one or two $(C_1\text{-}C_4)$ alkyl groups.

4. A compound according to claim 1 where n is zero.

5. A compound according to claim 1 where X is CH and $R_1$ is in the 2- or 3-position of the benzene.

6. A compound according to claim 4 where X is a nitrogen atom and the pyridine is substituted in the 2,6-positions.

7. A compound according to claim 2, where $R_4$, $R_5$ and $R_6$ are hydrogen atoms.

8. A compound selected from the group consisting of 7-(2-(4-(3-(Trifluoromethyl)phenyl)piperidino)ethyl)isoquinoline, its mono-N-oxide, its bis-N-oxide, its salts and its solvates.

9. A process for the preparation of a compound of formula (I) according to claim 1 which comprises carrying out a reductive alkylation of a compound of formula (II):

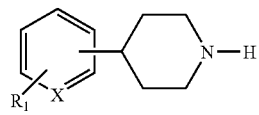

with an aldehyde of formula (III):

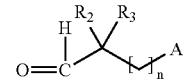

wherein $R_1$, X, $R_2$, $R_3$, n and A are as defined in claim 1, isolating the compound of formula (I) and optionally converting it to one of its salts or solvates or to its N-oxide derivatives.

10. A pharmaceutical composition, comprising, as active principle, a compound according to claim 1 together with a pharmaceutically acceptable carrier.

11. A composition according to claim 10, which comprises from 0.001 to 100 mg of active principle.

12. A compound according to claim 2 where n is zero.

13. A compound according to claim 3 where n is zero.

14. A compound according to claim 12 where $R_2$ and $R_3$ are each H.

15. A compound according to claim 13 where $R_2$ and $R_3$ are each H.

16. A compound according to claim 14 where $R_1$ is a $CF_3$ group.

17. A compound according to claim 15 where $R_1$ is a $CF_3$ group.

18. A compound according to claim 14 where $R_1$ is a fluorine atom.

19. A compound according to claim 15 where $R_1$ is a fluorine atom.

20. A compound according to claim 16 wherein X is CH and $R_1$ is in the 2- or 3-position of the benzene.

21. A compound according to claim 17 wherein X is CH and $R_1$ is in the 2- or 3-position of the benzene.

22. A compound according to claim 20 wherein $R_1$ is in the 3-position of the benzene.

23. A compound according to claim 21 wherein $R_1$ is in the 3-position of the benzene.

24. A compound according to claim 12 where X is a nitrogen atom and the pyridine is substituted in the 2,6-positions.

25. A compound according to claim 12 where $R_4$, $R_5$ and $R_6$ are hydrogen atoms.

26. A compound according to claim 20 where $R_4$, $R_5$ and $R_6$ are hydrogen atoms.

27. A compound according to claim 1 selected from the group consisting of:
- 7-(2-(4-(3-(trifluoromethyl)phenyl)piperidino)ethyl)isoquinoline;
- 6-(2-(4-(3-(trifluoromethyl)phenyl)piperidino)ethyl)-1,2,3,4-tetrahydroisoquinoline;
- 6-(2-(4-(3-(trifluoromethyl)phenyl)piperidino)ethyl)-1,2,3,4-tetrahydroquinoxaline;
- 6-(2-(4-(3-(trifluoromethyl)phenyl)piperidino)ethyl)benzofuran;
- 6-(2-(4-(3-(trifluoromethyl)phenyl)piperidino)ethyl)quinoline;

6-(2-(4-(3-(trifluoromethyl)phenyl)piperidino)ethyl)benzothiophene;
6-(2-(4-phenylpiperidino)ethyl)isoquinoline;
6-(2-(4-(3-(trifluoromethyl)phenyl)piperidino)ethyl)isoquinoline;
6-(2-(4-(6-(trifluoromethyl)pyrid-2-yl)piperidino)ethyl) isoquinoline; and
the acid-addition salts and solvates thereof.

28. A pharmaceutical composition, comprising, as active principle, a compound according to claim 12 together with a pharmaceutically acceptable carrier.

29. A pharmaceutical composition, comprising, as active principle, a compound according to claim 20 together with a pharmaceutically acceptable carrier.

30. A pharmaceutical composition, comprising, as active principle, a compound according to claim 27 together with a pharmaceutically acceptable carrier.

31. A pharmaceutical composition, comprising, as active principle, a compound according to claim 8 together with a pharmaceutically acceptable carrier.

32. A method of producing analgesia in a patient in need thereof which comprises administering to said patient an analgesically effective amount of a compound according to claim 1.

33. A method of producing analgesia in a patient in need thereof which comprises administering to said patient an analgesically effective amount of a compound according to claim 12.

34. A method of producing analgesia in a patient in need thereof which comprises administering to said patient an analgesically effective amount of a compound according to claim 20.

35. A method of producing analgesia in a patient in need thereof which comprises administering to said patient an analgesically effective amount of a compound according to claim 27.

36. A method of producing analgesia in a patient in need thereof which comprises administering to said patient an analgesically effective amount of a compound according to claim 8.

* * * * *